United States Patent [19]

Kim et al.

[11] Patent Number: 5,505,956
[45] Date of Patent: Apr. 9, 1996

[54] MEDICINAL ADHESIVE FOR PERCUTANEOUS ADMINISTRATION

[75] Inventors: Jung J. Kim; Woo Y. Lee, both of Anyang-shi; Jong W. Ahn, Seoul; Sang H. Han, Suwon-shi, all of Rep. of Korea

[73] Assignee: Pacific Chemical Co., Ltd., Seoul, Rep. of Korea

[21] Appl. No.: 186,925

[22] Filed: Apr. 1, 1994

Related U.S. Application Data

[63] Continuation-in-part of Ser. No. 982,972, Nov. 30, 1992.

[51] Int. Cl.$^6$ ..................................................... A61F 13/00
[52] U.S. Cl. ............................................. 424/448; 424/449
[58] Field of Search ..................................... 424/448, 449

[56] References Cited

U.S. PATENT DOCUMENTS

| | | | |
|---|---|---|---|
| 3,551,554 | 12/1970 | Herschler | 424/7 |
| 3,989,816 | 11/1976 | Rajadhyaksha | 424/60 |
| 4,031,894 | 6/1977 | Urquhart et al. | 128/168 |
| 4,316,893 | 2/1982 | Rajadhyaksha | 424/180 |
| 4,405,616 | 9/1983 | Rajadhyaksha | 424/244 |
| 4,537,776 | 8/1985 | Cooper | 514/424 |
| 4,695,465 | 9/1987 | Kigasawa et al. | 424/449 |
| 4,698,062 | 10/1987 | Gale et al. | 604/897 |
| 4,814,168 | 3/1989 | Sablotsky et al. | 424/78 |
| 4,844,903 | 7/1989 | Seth | 424/448 |
| 4,879,118 | 11/1989 | Senuma et al. | 424/448 |
| 4,938,964 | 7/1990 | Sakai et al. | 424/443 |
| 5,176,916 | 1/1993 | Yamanaka et al. | 424/448 |
| 5,413,794 | 5/1995 | Suzuki | 424/449 |

OTHER PUBLICATIONS

E. R. Cooper, "Increase Skin Permeability . . . " Jour. of Pharmaceutical Science, vol. 73 No. 8 Aug. 1984, pp. 1153–1156.

D. Patel et al, "Comparative study of propylene glycol . . . " Journal of the Society of Cosmetic Chemists, 36 (Jul./Aug. 1985), pp. 303–311.

*Primary Examiner*—D. Gabrielle Phelan
*Attorney, Agent, or Firm*—Nixon & Vanderhye

[57] ABSTRACT

Disclosed herein is a medicinal adhesive for percutaneous administration of a drug consisting of a support (backing layer), an adhesive layer comprising an oil-soluble drug, an adhesive resin, a penetration enhancer, a water-absorptive material and a lenitive agent, and a separate liner, charaterized in that the adhesive layer has a laminated structure having 2 to 5 layers and each layer has different water absorption capacities, and the drug is a oil-soluble, non-steroidal drug. For the adhesive of the present invention, the lowest layer which is to be contacted with the skin has the lowest water absorption capacity and the most upper layer in contact with the support has the highest water absorption capacity, or vice versa.

4 Claims, 1 Drawing Sheet

MEDICINAL ADHESIVE FOR PERCUTANEOUS ADMINISTRATION

This application is a continuation-in-part of Application Serial No. 07/982,972, filed on Nov. 30, 1992, now pending.

BACKGROUND OF THE INVENTION

1. Field of the Invention

The present invention relates to a medicinal patch which continuously delivers a certain amount of oil-soluble drugs through the skin or mucous membranes. More specifically, the present invention relates to a medicinal patch which dissolves the maximum level of drug in the adhesive layer contacting with the skin and delivers percutaneously the necessary amount of drug and enhances the percutaneous penetration of drug.

2. Description of the Prior Art

It has been widely used to deliver drugs (physiologically active agents) through the skin by employing a patch, a sort of percutaneous administrating preparations, for the purpose of the systemic or topical delivery of drugs. These methods of percutaneous administration offers many advantages over the traditional oral administration of drugs. For example, in the method of oral administration, a great level of drug is degraded by the metabolism in the liver prior to exhibiting its efficacy at the target site. However, in the method of percutaneous administration, the efficacy of absorbed drug is not seriously degraded by the metabolism in the liver because the absorbed drug does not pass through the liver before its circulation in the body. Particularly in the case of non-steroidal anti-inflammatory agents, their percutaneous administration gives an advantage of reducing the risk of damage to the gastrointestine which frequently occurs by the oral administration.

Based on the above-mentioned advantages, recently, studies on the transdermal drug delivery system which overcomes the first-pass effect or gastrointestinal damage induced in the oral administration and enhances the effectiveness and safety of drugs have been widely proceeded and, as a result, dermal compositions containing nitroglycerin, scopolamine and the like had been on the market.

In the meanwhile, many drawbacks of the above transdermal drug delivery system have also been indicated in connection with the difficulty in applying it to various drugs. Because the human skin serves as a barrier to the invasion of pathogens and toxic materials, it is highly impermeable. Accordingly, extensive attempts have been made for the purpose of enlarging the utility of transdermal delivery system and enhancing penetration through the skin.

It is possible to reduce the side effects caused by an administration of large amount of drug in a short time by regulating the absorption of the drug. It is also possible to maintain a constant level of drug in blood over a prolonged period by decreasing the frequency of administration.

However, a percutneous administration of drug frequently causes poor bioavailability due to the difficulty of penetration of the drug across the skin. To solve this problem, attempts to increase the absolute amount of drug in a patch to a level of ensuring the percutaneous absorption of necessary amounts have been made. For example, preparations for percutaneous admistration which comprise drug dissolved in bases for patch, ointment, cream and the like to a level exceeding the saturation concentration and dispersed in the form of recrystallized minute particles had been reported. If the patch of this type is applied on the skin surface, the drug dissolved in base is absorbed percutaneously and then, the drug existed in the form of minute particles is gradually dissolved and supplemented the absorbed drug. However, in practical, the drug existed in the form of minute particles is scarcely dissolved in the base and consequently the absorption rate of the drug across the skin is not relatively high.

Alternative methods of enhancing the percutaneous absorption of drug by occlusion have been also attempted. For example, methods for enhancing the percutaneous absorption of active agents by selecting substantially water-impermeable film as a backing layer of patch had been reported. However, these methods also have disadvantages that the sweat may arise skin-irritation and the patch is readily peeled off from the skin by the sweat. In order to eliminate the above problems, a plaster employing highly water-permeable materials such as non-woven fabric or hygroscopic urethane was proposed. However, these plasters have also failed in delivering the required amount of drug across the skin.

To reduce the skin-irritation and improve the feeling of adhesiveness, methods of employing water-soluble vehicle such as gelatin, polyvinylalcohol, dextrin, arabic gum, carboxymethyl cellulose, methylcellulose, hydroxy ethyl cellulose, polyvinylpyrrolidone, sodium alginate, sodium polyacrylate and the like have been also proposed. However, since the patches prepared by the above methods show poor skin-adhesiveness, they can not be applied alone on the skin and must be used together with a fabric applied adhesive and moreover, the efficacy of delivering drug across the skin is not sufficient.

U.S. Pat. No. 4,814,168 disclose a dermal composition suitable for use in the transdermal delivery of drugs, which composition permits a high loading of medicament into the formulation while maintaining acceptable shear, tack and peel as adhesive properties. The composition of the patent comprises a drug, a multi-polymer comprising vinyl acetate and ethylene monomers; a rubber and a tackifying agent.

U.S. Pat. No. 5,176,916 discloses an adhesive comprising a base mainly composed of a hydrophobic polymer in which a medicinal ingredient which is difficult to absorb percutaneously; for example a medicinal ingredient having relatively high hydrophilicity, is incorporated and water as a solubilizer is further contained. According to the patent, water is incorporated as a solubilizer in an amount necessary for making the plaster layer a W/O type.

However, the adhesive of U.S. Pat. No. 5,176,916 fits for relatively highly hydrophilic drugs and is not suitable for oil-soluble drugs, for example non-steroidal anti-inflammatory drugs since it contains water.

In these circumstances, the present inventors have made extensive studies for the purpose of providing a adhesive suitable for oil-soluble drugs which makes it possible to stably release the drug and sustain the pharmacological effects over a long period and as a result thereof found that the above purpose can be accomplished by a adhesive containing multilayered adhesive layer of which each layer has different water absorption capacity.

SUMMARY OF THE INVENTION

Thus, an object of the present invention is to provide a medicinal adhesive for percutaneous administrating oil-soluble, non-steroidal drug consisting of a water-impermeable backing layer, an adhesive layer comprising an oil-soluble drug, an adhesive resin, a penetration enhancer, a water-absorptive material and a lenitive agent, and a separate liner, charaterized in that the adhesive layer has a laminated structure having 2 to 5 layers and each layer has different water absorption capacity, and the lowest layer which is to be contacted with the skin has the lowest water absorption capacity and the most upper layer in contact with the backing layer has the highest water absorption capacity.

Another object of the present invention is to provide a medicinal patch for percutaneous administration consisting of a water-permeable backing layer, an adhesive layer comprising an oil-soluble drug, an adhesive resin, a penetration enhancer, a water-absorptive material and a lenitive agent, and a separate liner, charaterized in that the adhesive layer has a laminated structure having 2 to 5 layers and each layer has different water absorption capacity, and the lowest layer which is to be contacted with the skin has the highest water absorption capacity and the most upper layer in contact with the backing layer has the lowest water absorption capacity.

DETAILED EXPLANATION OF THE INVENTION

Figure 1:
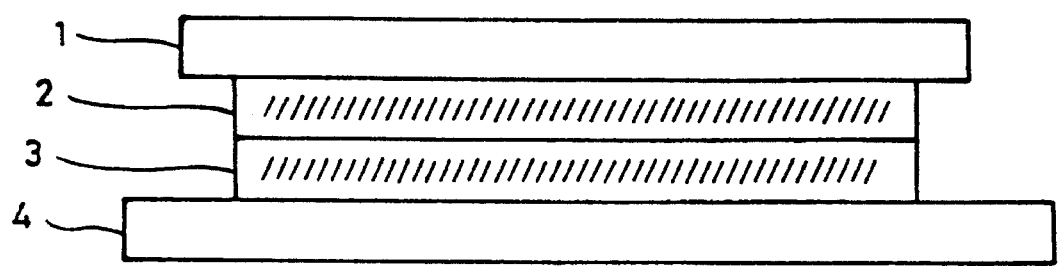
FIG. 1 is a cross-sectional view of the transdermal skin patch of the present invention having a multilayer laminated structure including a backing layer 1, an upper adhesive layer 2, a lower adhesive layer 3 and a liner layer 4.

The drug in the plaster is transdermally absorbed into the skin based on the difference of the drug concentrations between in the plaster and in the skin. In practice, the drug is absorbed through the stratum corneum by way of the following steps:

(1) Diffusion in a plaster;
(2) Partition from the vehicle to the surface of stratum corneum;
(3) Diffusion in the stratum corneum;
(4) Partition from the stratum corneum to the lower epidermal tissue;
(5) Diffusion in the epidermic and dermic layers; and
(6) Transfer from the dermis to the blood vessel.

It is generally considered that the process of the transdermal absorption of drug is divided into the diffusion process and the partition process. The diffusion can be described and calculated by Fick's the first law which shows the relationship between the concentration gradient and the penetration flux of drug and Fick's the second law which shows the change of drug concentration at a certain locus as a function of time.

$$J/A = -D\,C/x \quad \text{Fick's the first law}$$

$$C/t = D^2 C/x^2 \quad \text{Fick's the second law}$$

wherein
A=drug-diffused area
C=drug concentration
D=diffusion coefficient
J=speed of penetration
t=time
x=location The transdermal penetration effect of a drug is determined, in many cases, by the penetration flux at the steady-state and the penetration flux at the steady-state(J) can be described by:

$$J = ACvKD/L$$

wherein
Cv=drug concentration in the vehicle,
K=partition coefficient of the drug between the skin and the vehicle,
L=effective skin thickness
A & D=the same as defined above In addition, the penetration coefficient(Kp) can be described by:

$$Kp = KD/L$$

wherein K, D and L represent the same as defined above.

As can be seen in the above, it is advantageous to increase the drug concentration in the adhesive in order to deliver large amounts of the drug through the skin. However, the amount of drug which can be loaded in the adhesive is limited.

According to the present invention, as one of the means to increase the drug solubility in the adhesive layer and reduce skin irritation, the drug concentration in the adhesive layer is adjusted to a level of the maximum value by selecting the adhesive resin having similar solubility parameter with the drug. As the most suitable adhesive for the abovementioned purpose, acrylic adhesives are included. The acrylic adhesives are advantageous in controlling the water content and the drug solubility in the adhesive layer since they are easy to regulate the incorporation ratio of the monomers to be polymerized. However, when a plaster comprising the above adhesive resins is applied on the skin, the solubility of drug in the adhesive layer is changed as the water content in the adhesive layer is increased due to the water transpired from the skin as compared with that of immediately after the patch was prepared, and the saturation solubility of the drug is also changed. Consequently, the solubility of the drug shows significant difference with the practical view and at the same time, the amount of the drug delivered through the skin and the adhesive property of the adhesive are seriously decreased.

To overcome the above-mentioned problems, the present invention employs an adhesive comprising laminated adhesive layers, each having different water absorption capacity and containing no water. 2 to 5 adhesive layers may be laminated to form a adhesive multi-layer in which the lowest layer which is to be contacted with the skin has the lowest water absorption capacity and the most upper layer in contact with the backing layer has the highest water absorption capacity. Or, 2 to 5 adhesive layers may be laminated to form a adhesive multi-layer in which the lowest layer which is to be contacted with the skin has the highest water absorption capacity and the most upper layer in contact with the backing layer has the lowest water absorption capacity.

With regard to FIG. 1, the adhesive consists of a support(1), a higher adhesive layer(2), a lower adhesive layer(3) and a separate liner(4).

As the backing layer(1) of the adhesive, any supporting materials which are typically used in the art may be employed. Examples of such backing materials include cellulose acetate, ethyl cellulose, polyethylene terephthalate, plasticized vinyl acetate-vinylchloride copolymer, nylon, ethylene-vinyl acetate copolymer, plasticized polyvinylchloride, polyurethane, polyethylene, polyvinylidene chloride, aluminum and the like. These materials may be used, for example, in the form of a mono-layered sheet(film) or a two or more layered laminate. In addition to aluminum, cotton fabric or non-woven fabric may be also used as the backing layer.

When the backing layer(1) is made from a water-impermeable materials and controlled release of drug is desired, the lower adhesive layer(3) has a lower water absorption capacity than that of the higher adhesive layer(2). In this case, the water transpired from the skin after the adhesive is applied on the skin moves to the lower adhesive layer(3) which contains water absorptive materials and the water in the layer(3) gradually moves into the higher adhesive layer(2) which has a higher water absorption capacity than that of the lower adhesive layer(3). At an equilibrium state, the higher adhesive layer(2) retains more water than the lower adhesive layer(3). At the same time, the drug in the lower adhesive layer(3) absorbed into the skin, and the more water migrates to the lower(3) and then higher(2) layers the faster the drug absorbed into the skin. Accordingly, since the water and other water-soluble excretions from the skin migrate into upper layers, the lowest layer which is in contacting with the skin always retains constant amount of drug and moisture, thereby reducing the skin irritation due to sweat or other excretions.

Alternatively, when the backing layer(1) is made from the semipermeable orpermeable materials such as non-woven fabric, cotton fabric or any other air-permeable plastic film, the upper layer(2) has a considerably lower water absorption capacity than that of the lower layer(3) to prevent the migration of water evaporated from the skin to the upper layer(2) on order to attain a burst transdermal absorption of drug. For this purpose, the upper layer(2) may be made from a rubber resin and the lower layer(3) may be made from a acrylic resin and has water absorption capacity of about 1 to 5%.

The multi-layer adhesive according to the invention, of which water retention in each layer may be controlled its water retention, may be applied to control the release rate of the drug.

The adhesive of the invention have a laminated adhesive layer having 2 to 5 layers. The thickness of each layer is typically 2 to 150 µm, preferably 10 to 100 µm. And the overall thickness of the laminated adhesive layer is typically 30 to 500 µm, preferably 30 to 200 µm.

The backing layer of the adhesive may be made from a mono- or multi-layered polyethylene, polypropylene, polyethyleneterephtalate, or non-woven fabric, cotton fabric or plastic films.

The separate liner of the adhesive of the invention may be any one of those employed for the percutaneous preparations and is, for example, a film incorporated with silicone- or fluoro-type releasing agent.

The laminated adhesive layer of the adhesive of the invention may comprise a drug, an adhesive resin, a penetration enhancer, a water absorptive material, a lenitive and a tackfying agent.

As an adhesive resin, there may be included, but not intended to be limited thereto, silicone polymers, natural or synthetic rubbers, acrylic polymers.

Particularly, for the present invention, the acrylic polymers such as co(polymer) of $C_4$–$C_{18}$ aliphatic alcohol with (meth)acrylic alkyl ester or the copolymer of (meth)acrylic alkyl ester having $C_4$–$C_{18}$ alkyl, (meth)acrylic acid and/or other functional monomers are preferably employed as the adhesive.

Examples of the (meth)acrylic alkyl ester may include butyl acrylate, isobutyl acrylate, hexyl acrylate, octyl acrylate, 2-ethylhexyl acrylate, iso-octyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, iso-octyl methacrylate, decyl methacrylate, etc.

Examples of the functional monomers may include a monomer containing hydroxyl group, a monomer containing carboxyl group, a monomer containing amide group, a monomer containing amino group. Examples of the monomer containing hydroxyl group may include hydroxy alkyl (meth) acrylate such as 2-hydroxyethyl (meth)acrylate, hydroxypropyl (meth) acrylate and the like. Examples of the monomer containing carboxyl group may include $\alpha$-$\beta$ unsaturated carboxylic acid such as acrylic acid, methacrylic acid and the like; maleic mono alkyl ester such as butyl malate and the like; maleic acid; fumaric acid; crotonic acid and the like; and anhydrous maleic acid. Examples of the monomer containing amide group may include alkyl (meth)acrylamide such as acrylamide, dimethyl acrylamide, diethyl acrylamide and the like; alkylethylmethylol (meth) acrylamide such as butoxymethyl acrylamide, ethoxymethyl acrylamide and the like; diacetone acrylamide; vinyl pyrrolidone; dimethyl aminoacrylate.

In addition to the above exemplified monomers for copolymerization, vinyl acetate, styrene, $\alpha$-methylstyrene, vinyl chloride, acrylonitrile, ethylene, propylene, butadiene and the like may be employed.

Examples of the rubber which may be used as an adhesive resin incorporated into the adhesive layer in accordance with the present invention may include natural gum, polyisoprene, polyisobutylene, styrene-butadiene-styrene copolymer, styrene-isoprene-styrene copolymer, styrene-ethylene/propylene-styrene copolymer, styrene-ethylene/butylene-styrene copolymer, polyvinyl ether, polyurethane, polybutadiene, styrene-butadiene copolymer, styrene-isoprene copolymer, styrene-isoprene-butylene block copolymer and the like.

As the silicone resins, there may be included silicone gum such as polyorgano siloxane.

When an acrylic polymer is employed as the adhesive resin for the adhesive layer, the adhesive layer may contain (meth)acrylic alkyl ester incorporated in an amount of 50% by weight or above.

Further, for the purpose of increasing or decreasing the water absorption capacity of the adhesive layers, the acrylic polymer may be copolymerized with a hydrophilic monomer, a monomer containing carboxyl group, a monomer containing amide group, a monomer containing amino group and the like. Further, the rubbery or silicone resins are employed as the adhesive resin, there may be incorporated into the adhesive layer with a tackifying agent or other additives.

Alternatively, the water absorption capacity of the adhesive layer can be also regulated by incorporating therein highly water-absorptive polymers, polyols and water-absorptive inorganic materials. Examples of the highly water-absorptive resins may include mucopolysaccharides such as hyaluronic acid, chondroitin sulfate, dermatan sulfate and the like; polymers having a large number of hydrophilic groups in the molecule such as chitin, chitin derivatives, starch and carboxy-methylcellulose; and semi-synthetic and synthetic highly water-absorptive polymers such as polyacrylic, polyoxyethylene, polyvinyl alcohol and polyacrylonitrile. Examples of the water-absorptive inorganic materials, which may incorporated into the adhesive layer to regulate its water absorptive capacity, may include powdered silica, zeolite, powdered ceramics and the like.

Examples of the polyols may include propylene glycol, glycerin, sorbitol and the like.

These substances for regulating the water-absorption capacity of the adhesive layer may be employed in an amount of 0.1–40% by weight, preferably 1–20% by weight.

The adhesive layers may contain a tackfying agent and as a tackfying agent, there may be included, but not intended to be limited thereto, rosin esters, polyterpene resin, petroleum resin, terpene phenol resin.

The adhesive layers may contain penetration enhancers, for example dodecyl sulfoxide mono- or dimethyl acetamide, N-hydroxy ethyl lactide, higher fatty acid ester, salicylic acid, sorbitol, urea, glycerin, squalene, squalane, acetylated lanolin, cetyl laurate, olive oil, castor oil, lauric acid, oleic acid, lauryl alcohol, oleyl alcohol, ethoxystearyl alcohol, liquid paraffin, vaseline, camphor, glycerin fatty acid ester, fatty acid mono- (or di-) ethanolamide, ethylene glycol mono ethyl ether, polyoxyethylene alkyl ether, polyoxyethylene alkyl ester, polyoxypropylene alkyl ether, propylene glycol mono(di)alkyl ester, propylene glycol monolaurate, polyoxyethylene lauryl ether, pyrrolidone derivatives and the like. The amount of the penetration enhancer is 0.1 to 40% by weight, preferably 1 to 20% by weight.

The present inventors had found that when the drug is of oil-soluble type, for example ketoprofen, a hydrophobic surfactant having a HLB value of less than 10, for example propylene glycol monolaurate or polyoxyethylene alkyl ether wherein the mole number of ethylene oxide is less than 7 is preferred as a penetration enhancer, since they help the migration of water transpired from the skin across the adhesive layers.

The adhesive layer in accordance with the present invention also include a lenitive agent, for example alpha-bisabolol, camomile oil, allantoin and d-panthenol. The lenitive agents may be present in an amount of 0.01–10% by weight, preferably 0.1–5% by weight.

The adhesive may further include a plasticizer, a filler, an antioxidant or a preservative, which may be commonly employed for the production of a medicinal plaster. As an antioxidant, tocopherol, tocopheryl acetate, BHA, BHT and the like are employed and the preservatives such as ethyl paraben, methyl paraben and butyl paraben may be employed.

The drug which is incorporated into the adhesive layers is oil-soluble type and have the solubility that it requires 30 ml, preferably 100 ml, more preferably more than 1000 ml of water to dissolve 1 g or 1 ml of drug. In this regard, nonsteroidal anti-inflammatory drugs, specifically methyl salicylate, salicylic acid, ibuprofen, ketoprofen, flurbiprofen, indomethacin, diclofenac, flufenamic acid, naproxen, mefenamic acid, fenoprofen, fenclofenax, piroxicam and the precursors thereof can be used. The drug may be incorporated in an amount of 0.1–40% by weight.

Examples of the water-absorptive materials which may be employed to improve the absorptive capacity of the adhesive layer may include polyvinyl alcohol, polyvinyl pyrrolidone, alginic acid, hyaluronc acid, cellulose, chitin and their derivatives, zinc oxide, calcium oxide, silica, kaolin, talc or titanium oxide. The materials may be present in an amount of 0.1–30% by weight, preferably 0–10% by weight.

PREFERRED EMBODIMENT OF THE INVENTION

The present invention will be embodied by way of the following examples. However, these examples are provided for the illustration purpose only and should not be construed as limiting the scope of the invention, which is properly delineated in the accompanying claims.

EXAMPLE 1

(A) Preparation of adhesive resin(1)

To a reaction vessel equipped with a reflux condenser and a stirrer, 97.4 parts of 2-ethylhexyl acrylate, 2.5 parts of methacrylic acid, 0.1 parts of polyethylene glycol diacrylate, 1.0 parts of benzoyl peroxide and 100 parts of ethyl acetate were added and, under nitrogen atmosphere, the polymerization reaction was carried out under stirring.

In order to regulate the polymerization degree, 100 parts of ethyl acetate was added to the reaction mixture gradually during the polymerization reaction, and the reaction was conducted for 9 hours. The polymerization degree was 99.9%.

To the resulting polymer solution, ethyl acetate was added to adjust the solid content to about 40% by weight. Finally, there was obtained a copolymer of ehtylhexylacrylate, methacrylic acid and polyethyleneglycol dimethacrylate, which is employed as an adhesive resin.

(B) Preparation of adhesive resin(2)

Under the same conditions as described above, the copolymerization reaction was carried out by employing 70 parts of 2-ethylhexylacrylate, 10 parts of acrylic acid, 1.0 parts of benzoyl peroxide (BPO) and 20 parts of vinyl acetate.

The polymerization degree was more than 99.9%. Aluminum acetate was added to the polymerization product under stirring(200 rpm) to obtain a self-curable product. To the resulting polymer solution, ethyl acetate was added to adjust the solid content to about 40% by weight.

Finally, there was obtained a copolymer of ehtylhexylacrylate, methacrylic acid and polyethyleneglycol dimethacrylate, which is employed as an adhesive resin. (C) Preparation of the adhesive lower layer(3) in FIG. 1.

To the adhesive resin(1) obtained in the above, ketoprofen was added in an amount of 20% by weight based on the solid content and dissolved therein to a concentration exceeding the saturation solubility.

The resulting mixture was coated on to the siliconetreated PET separate liner. At this time, the amount of the mixture was adjusted in such a way that the coating thickness after drying become 50 μm. The water absorption capacity of this adhesive layer was 1.9% in terms of water content.

(D) Preparation of the adhesive upper layer(2) in FIG. 1.

To the adhesive resin(2) obtained in the above, ketoprofen was added in an amount of 20% by weight and dissolved therein to a concentration exceeding the saturation solubility. The resulting mixture was coated on to the silicone treated releasing paper to a thickness of 30 μm after drying. The water absorption capacity of this adhesive layer was 3.6% in terms of water content.

(E) Fabricaton of adhesive

The upper adhesive layer(2) was adhered by rolling onto a support(polyethylene film) and then, the lower adhesive layer(3) was laminated thereonto to produce a medicinal adhesive of the present invention depicted in FIG. 1. Thereafter, the adhesive was dried by allowing to stand at normal temperature for 15 minutes and then at 90° C. for 10 minutes.

EXAMPLE 2

(A) Preparation of the adhesive layers (2) and (3)

To the adhesive resin(1) obtained in Example 1(A), ketoprofen was added in an amount of 25% by weight based on the solid content and dissolved therein to a concentration exceeding the saturation solubility.

After hyaluronic acid powder of 5% by weight was added to the resulting mixture and dispersed uniformly therein to give an adhesive layer(3). The adhesive layer(3) has a water absorption capacity of 2.1% in terms of water content.
(B) Fabricaton of adhesive The adhesive layer(3) was coated on to the silicone-treated releasing paper to a thickness of 40 μm after drying.

Besides, the adhesive layer(2) obtained in Example 1(D) was adhered by rolling onto a support(polyester film) and then, the above lower adhesive layer(3) was laminated thereonto to produce a medicinal adhesive of the present invention depicted in FIG. 1. Thereafter, the adhesive was dried by allowing to stand at normal temperature for 15 minutes and then at 90° C. for 10 minutes.

EXAMPLE 3

(A) Preparation of an adhesive layer(3)

To the adhesive resin(1) obtained in Example 1(A), ketoprofen was added in an amount of 35% by weight based on the solid content and dissolved therein to a concentration exceeding saturation solubility. To the resulting mixture, polyoxyethylene(E.O.=3) lauryl ether of 10% by weight as a penetration enhancer and tocopherol acetate of 0.5% by weight as an antioxidant were added and dissolved. Then, colloidal silica of 3% by weight was incorporated as a tackifying agent to reduce the decrease in adhesiveness due to the addition of the penetration enhancer.

The adhesive layer(3) obtained in the above, which has a water absorptive capacity of 2.0% in terms of water content, was coated on to a releasing paper to a thickness of 60 μm after drying.
(B) Preparation of an adhesive layer(2)

To the adhesive resin(2) obtained in Example 1(B), ketoprofen was added in an amount of 23% by weight based on the solid content and dissolved to a concentration exceeding the saturation solubility. After 10% by weight of polyoxyethylene(E.O=3) lauryl ether was added to the mixture as a penetration enhancer, 0.5% by weight of tocopheryl acetate as an antioxidant was also added and dissolved. Thus obtained adhesive layer(2) has a water absorption capacity of 3.6% in terms of water content.
(C) Fabrication of adhesive The adhesive layer(3) was adhered by rolling to a polyester film and the above adhesive layer(2) was laminated thereon to produce a medicinal adhesive of the present invention depicted in FIG. 1. Thereafter, the adhesive was dried by allowing to stand at normal temperature for 17 minutes and then at 86° C. for 10 minutes.

EXAMPLE 4

(A) Preparation of adhesive layer(3)

To the adhesive resin(2) obtained in Example 1(B), ketoprofen was added in an amount of 28% by weight based on the solid content and dissolved therein to a concentration exceeding saturation solubility.

After 10% by weight of propylene glycol monooleate as a penetration enhancer was added to the mixture, 0.5% by weight of tocopherol as an antioxidant and 2% by weight of bisabolol as a lenitive agent were added thereto.

Thereafter, 3% by weight of zinc oxide powder(diameter of particles 5–15 μm) as a water content controlling agent was uniformly dispersed therein. Thus obtained adhesive layer(3) has a water absorptive capacity of 4.2% in terms of water content and was coated on to a releasing paper to a thickness of 70 μm after drying.
(B) Preparation of an adhesive layer(2)

To the adhesive resin(1) obtained in Example 1(A), ketoprofen was added in an amount of 26% by weight based on the solid content and dissolved to a concentration exceeding the saturation solubility. After 10% by weight of polyoxyethylene(E.O=3) lauryl ether was added to the mixture as a penetration enhancer, 0.5% by weight of tocopheryl acetate as an antioxidant was also added and dissolved. Thus obtained adhesive layer(2) has a water absorption capacity of 1.4% in terms of water content.
(C) Fabrication of adhesive The adhesive layer(2) was adhered by rolling to a nonwoven fabric and the above adhesive layer(3) was laminated thereon to produce a medicinal adhesive of the present invention depicted in FIG. 1. Thereafter, the adhesive was dried by allowing to stand at normal temperature for 17 minutes and then at 86° C. for 10 minutes.
Quantitative determination of the water content Water was extracted from the pieces of the size of 5×5cm$^2$ cut out from each adhesive layers which are coated into a polyester film to a thickness of 100 μm after drying of Examples 1 to 4 with anhydrous methanol with sufficient care prohibiting entry of external moisture and subjected to chromatography to quantitatively determine the water content in the adhesive layers. Experimental Example 1

Percutaneous penetration test

Using a male guinea pig weighing about 350 g, the abdominal hair was removed using a hair clipper Then, a part of the abdominal skin was excised, stored in a refrigerator (below −20° C.) and used after thawing at needs.

The excised skin was placed in the middle of the Franz-type diffusion cell with its corneous side looking upward and the space below the cell was charged with 0.05M phosphate buffered saline(pH 7.4). The adhesives shown in Table 1 below were applied on the skin while the buffer solution-(receiver solution) was stirred at a constant speed of 600 rpm.

At varying intervals, a portion of the receiver solution was taken for the test and a fresh buffer solution was supplemented in the same amount as taken therefrom. From the test solution, the concentration of ketoprofen was determined by High Pressure Liquid Chromatography(HPLC).
Analysis condition for HPLC Column: $C_{18}$ μBondapak [Waters Chromatography, Inc., milton Massachusetts 01757 USA]

Mobile phase: 55:45 V/V mixture of methanol: 0.02M phosphate buffered solution(pH 4.0)

Flow rate: 1 ml/min.

Detector: 254 nm wave length ultraviolet

The results are shown in Table 2 below.

TABLE 1

Adhesive formulations used for the percutaneous penetration test

| Adhesive No. | Ketoprofen Conc. (%) | Propylene glycol monolaurate (%) | Polyoxyethylene(3) lauryl ether (%) | Glycerol monooleate (%) | Zinc oxide (%) | Tocopheryl acetate (%) |
| --- | --- | --- | --- | --- | --- | --- |
| 1 | 10 | | | | 5 | 1 |
| 2 | 20 | | | | 5 | 1 |
| 3 | 25 | | | | 5 | 1 |
| 4 | 30 | | | | 5 | 1 |
| 5 | 40 | | | | 5 | 1 |
| 6 | 10 | 10 | | | 5 | 1 |
| 7 | 10 | 20 | | | 5 | 1 |
| 8 | 30 | 10 | | | 5 | 1 |
| 9 | 10 | | 10 | | 5 | 1 |
| 10 | 10 | | | 10 | 5 | 1 |
| 11 | 20 | | 5 | | 5 | 1 |
| 12 | 20 | | | 5 | 5 | 1 |
| 13 | 10 | | | | 10 | 2 |
| 14 | 10 | | 5 | | 10 | 2 |
| 15 | 15 | | | 5 | 10 | 2 |

TABLE 2

Comparison of the penetration flux ratio of ketoprofen of the adhesives in Table 1

| Adhesive No. | Skin penetration Flux ($\mu m/cm^2/hr$) | Lag time (hrs) | Skin penetration flux ratio* |
| --- | --- | --- | --- |
| 1 | 15.5(2.62) | 2.19(0.31) | 1.00 |
| 2 | 20.7(3.01) | 1.96(0.41) | 1.34 |
| 3 | 24.5(2.87) | 1.93(0.45) | 1.58 |
| 4 | 31.7(1.71) | 1.47(0.21) | 2.05 |
| 5 | 34.6(2.30) | 1.38(0.39) | 2.23 |
| 6 | 26.8(3.68) | 1.95(0.51) | 1.73 |
| 7 | 35.7(2.96) | 2.01(0.47) | 2.30 |
| 8 | 45.3(4.17) | 1.58(0.40) | 2.92 |
| 9 | 34.2(3.91) | 1.94(0.52) | 2.21 |
| 10 | 36.2(4.25) | 2.09(0.63) | 2.34 |
| 11 | 33.2(3.75) | 1.68(0.37) | 2.14 |
| 12 | 35.2(3.75) | 1.96(0.31) | 2.26 |
| 13 | 20.5(2.15) | 2.53(0.74) | 1.32 |
| 14 | 34.4(1.78) | 1.57(0.45) | 2.22 |
| 15 | 35.1(2.35) | 1.64(0.76) | 2.26 |

Note:
*Each value is an average of 4(four) repeats
*The skin-penetration flux ratio was relatively calculated as taking 1.00 when the content of ketoprofen was 10% and no penetration enhancer was employed.

[Results]

The skin-penetration flux ratio of ketoprofen was increased when the content of ketoprofen in the adhesive layer was increased to a concentration exceeding the saturation solubility.

Contrary to the general phenomenon that when the penetration enhancer is incorporated into the adhesive layer by conventional techniques, the penetration enhancement of drug is reduced due to a sharp decrease of the adhesiveness, the adhesive layer according to the present invention retained its good adhesiveness.

Experimental Example 2

Skin primary irritation test

A adhesive prepared in the same manner as described in Example 1 was cut to the size of 2.5 cm² and after the separate liner was removed therefrom, the adhesive was applied on the forearm of a healthy man for 24 hours.

24 hours later, the adhesive was removed and, after 30 minutes, the level of the skin primary irritation was observed and estimated according to the following standard.

| Score | The level of irritation |
| --- | --- |
| 0 | No irritation |
| 1 | The minimum irritation |
| 2 | A little irritation (erythema) |
| 3 | Severe irritation (erythema, edema) |
| 4 | Extremely severe irritation (erythema, edema) |

By using the score of irritation, the reactivity was calculated according to the following equation :

$$\text{Reactivity}(\%) = \frac{\text{The sum of the number of } x \text{ Score reactor(s)}}{\text{The number of subjects} \times 4} \times 100$$

The results are shown in Table 3.

TABLE 3

Skin primary irritation test

| Adhesive No. | Ketoprofen Conc.(%) | Propylene glycol monolaurate (%) | Polyoxyethylene(3) lauryl ether(%) | Adhesive resin (1) (%) | bisabolol (%) | No. of subjects | Reactivity | Frequency of skin irritation occurance |
| --- | --- | --- | --- | --- | --- | --- | --- | --- |
| 1 | 10 | 10 | | 90 | | 17 | 2.9 | 2/17 |

TABLE 3-continued

| | | | Skin primary irritation test | | | | | |
|---|---|---|---|---|---|---|---|---|
| Adhesive No. | Ketoprofen Conc.(%) | Propylene glycol monolaurate (%) | Polyoxyethylene(3) lauryl ether(%) | Adhesive resin (1) (%) | bisabolol (%) | No. of subjects | Reactivity | Frequency of skin irritation occurance |
| 2 | 10 | | 10 | 80 | | 17 | 5.9 | 4/17 |
| 3 | 10 | 10 | | 80 | | 15 | 6.7 | 4/15 |
| 4 | 10 | 10 | | 79.5 | 0.5 | 15 | 5.0 | 3/15 |
| 5 | 10 | 10 | | 79 | 1 | 15 | 0.0 | 0/15 |
| 6 | 10 | 10 | | 78 | 2 | 15 | 0.0 | 0/15 |
| 7 | 10 | 10 | 20 | 75 | 5 | 15 | 5.0 | 3/15 |
| 8 | 20 | | | 58 | 2 | 17 | 4.4 | 3/17 |
| 9 | 10 | | 10 | 78 | 2 | 15 | 1.7 | 1/15 |
| 10 | 20 | | 10 | 69 | 1 | 17 | 0.0 | 0/17 |

As can be seen from the above Table 3, the adhesives of the present invention arise no skin irritation.

Comparative Example 1

The adhesive layer(2) prepared in Example 1(D) was singly coated on a separate liner and then laminated onto a polyethylene film to produce a mono-layered adhesive.

Comparative Example 2

To the adhesive layer(1) prepared in Example 1(C), 5% by weight of tocopherol as an antioxidant, 10% by weight of propylene glycol monooleate as a penetration enhancer and 2% by weight of bisabolol as a lenitive agent were added and dissolved. The resulting mixture was coated on a releasing paper to a thickness of 70 μm and dried.

Experimental Example 3

Penetration test

By the same manner as described above in Experimetal Example 1, the adhesives of Examples 1–4 and Comparative examples 1–2 were tested and the results are shown in Table 4.

TABLE 4

| | Comparison of the skin penetration flux of ketoprofen | | |
|---|---|---|---|
| Adhesive (Example No.) | Skin penetration flux(μg/cm²/hr) | Lag time (hr) | Skin penetration flux ratio |
| Ex. 1 | 17.7(3.79) | 2.78 ± 0.74 | 1.97 |
| Ex. 2 | 15.6 ± 2.28 | 3.14 ± 1.45 | 1.73 |
| Ex. 3 | 27.4 ± 2.11 | 1.75 ± 1.23 | 3.04 |
| Ex. 4 | 18.8 ± 3.18 | 2.20 ± 0.79 | 2.09 |
| Comp. 1 | 9.0 ± 3.45 | 3.05 ± 1.05 | 1.00 |
| Comp. 2 | 22.4 ± 2.79 | 1.67 ± 0.68 | 2.49 |

Experimental Example 4

Skin primary irritation test

By the same manner as described above in Experimental Example 2, the adhesives prepared in Examples 1–4 and Comparative examples 1–2 were tested and the results are shown in Table 5.

TABLE 5

| Adhesive (Example No.) | No. of subjects | Reactivity (%) | Frequency of skin-irritation occurance |
|---|---|---|---|
| Ex. 1 | 13 | 3.8 | 2/13 |
| Ex. 2 | 13 | 1.9 | 1/13 |
| Ex. 3 | 13 | 3.8 | 2/13 |
| Ex. 4 | 13 | 0.0 | 0/13 |
| Comp. 1 | 13 | 3.8 | 2/13 |
| Comp. 2 | 13 | 1.9 | 1/13 |

What is claimed is:

1. A transdermal skin patch to adhere to a patient's skin, said skin patch comprising (1) a water-impermeable support or backing layer, (2) a liner, and between the two, (3) a multilayer laminate of from 2 to 5 adhesive layers, each of said adhesive layers comprising an oil-soluble drug, an adhesive resin, a penetration enhancer, a water-absorptive material and a lenitive agent, wherein each adhesive layer contains no water and has a different water absorption capacity in which the lowest layer which is to be contacted with the skin has the lowest water absorption capacity and the most upper layer in contact with the backing layer has the highest water absorption capacity, and the drug is ketoprofen present in an amount of 0.1 to 40% by weight.

2. The transdermal skin patch as claimed in claim 1, wherein the water absorptive material is selected from the group consisting of polyvinyl alcohol, polyvinyl pyrrolidone, alginic acid, hyaluronc acid, cellulose, chitin, zinc oxide, calcium oxide, silica, kaolin, talc and titanium dioxide and is present in an amount of 0.1–30% by weight.

3. A transdermal skin patch to adhere to a patient's skin, said skin patch comprising (1) a water-permeable support or backing layer, (2) a liner, and between the two (3) a multilayer laminate having 2 to 5 adhesive layers, each of said adhesive layers comprising an oil-soluble drug, and adhesive resin, a penetration enhancer, a water-absorptive material and a lenitive agent, wherein each adhesive layer contains no water and has a different water absorption capacity in which the lowest layer which is to be contacted with the skin has the highest water absorption capacity and the most upper layer in contact with the backing layer has the lowest water absorption capacity and the drug is ketoprofen present in an amount of 0.1 to 40% by weight.

4. The transdermal skin patch as claimed in claim 3, wherein the water absorptive material is selected from the group consisting of polyvinyl alcohol, polyvinyl pyrrolidone, alginic acid, hyaluronc acid, cellulose, chitin, zinc oxide, calcium oxide, silica, kaolin, talc and titanium dioxide and is present in an amount of 0.1–30% by weight.

* * * * *

UNITED STATES PATENT AND TRADEMARK OFFICE
CERTIFICATE OF CORRECTION

PATENT NO. : 5,505,956
DATED : April 9, 1996
INVENTOR(S) : KIM et al

It is certified that error appears in the above-identified patent and that said letters patent is hereby corrected as shown below:

On the title page, Assignee should read:

[73] Assignee: Pacific Corporation and Pacific Pharmaceutical Co., Ltd.

Signed and Sealed this

Twenty-second Day of October, 1996

Attest:

BRUCE LEHMAN

*Attesting Officer*          *Commissioner of Patents and Trademarks*